United States Patent [19]
Graham

[11] Patent Number: 5,147,646
[45] Date of Patent: Sep. 15, 1992

[54] HYDROGEL CONTAINING ENVELOPES

[75] Inventor: Neil B. Graham, Glasgow, United Kingdom

[73] Assignee: National Research Development Corporation, London, England

[21] Appl. No.: 759,623

[22] Filed: Sep. 16, 1991

Related U.S. Application Data

[63] Continuation of Ser. No. 229,725, Aug. 5, 1988, abandoned, which is a continuation of Ser. No. 818,076, Jan. 13, 1986, abandoned, which is a continuation of Ser. No. 585,541, Mar. 2, 1984, abandoned.

[30] Foreign Application Priority Data

Mar. 2, 1983 [GB] United Kingdom ................ 8305797

[51] Int. Cl.$^5$ ...................... A01J 21/00; A01J 25/00; A21C 3/00; A21C 11/00
[52] U.S. Cl. .................................. 424/424; 424/425; 424/426; 424/443; 424/469; 424/470; 210/633; 210/634; 210/635; 210/642; 604/372; 604/374; 604/375
[58] Field of Search ...................... 424/14, 16, 19, 20, 424/22, 424, 425, 426, 443, 469, 470; 210/633, 635, 642, 634; 604/372, 374, 375, 369, 892

[56] References Cited

U.S. PATENT DOCUMENTS

| | | | |
|---|---|---|---|
| 3,280,549 | 10/1966 | Hsu | 60/17 |
| 3,451,926 | 6/1969 | Haas | 210/59 |
| 3,551,556 | 12/1970 | Kliment et al. | 424/19 |
| 3,745,659 | 7/1973 | Hsu | 33/126.7 R |
| 3,951,812 | 4/1976 | Hsu | 210/282 |
| 3,975,350 | 8/1976 | Hudgin | 524/108 |
| 4,053,398 | 10/1977 | Venema | 210/41 |
| 4,150,108 | 4/1979 | Graham | 424/19 |
| 4,207,890 | 6/1980 | Mamajek et al. | 128/223 |
| 4,267,295 | 5/1981 | Gallop et al. | 526/264 |
| 4,340,491 | 7/1982 | Lee | 8/137 |
| 4,419,236 | 10/1983 | Hsu | 210/282 |

FOREIGN PATENT DOCUMENTS

| | | |
|---|---|---|
| 513656 | of 0000 | Australia . |
| 1118430 | 7/1968 | United Kingdom . |
| 1204900 | 9/1970 | United Kingdom . |
| 1437835 | 6/1976 | United Kingdom . |
| 2086400 | 5/1982 | United Kingdom . |

OTHER PUBLICATIONS

Chem. Abs., 95, No. 10, 49345A.
Chem. Abs., 95, No. 4, 47886y.

*Primary Examiner*—Nathan M. Nutter
*Attorney, Agent, or Firm*—Oblon, Spivak, McClelland, Maier & Neustadt

[57] ABSTRACT

An envelope having flexible water-permeable or porous walls contains a quantity of particulate water-insoluble hydrogel. The quantity of hydrogel in the envelope is such that, when the hydrogel is fully swollen at 20° C., its volume is at least 66%, preferably at least 100%, of the maximum non-stretched internal volume of the envelope. Thus, the envelope according to the invention is limp and floppy under dry conditions but in a wet environment the hydrogel absorbs water and swells accordingly causing the envelope to swell and take on a more rigid configuration. The envelope is particularly useful for the administration of sustained release pharmaceutically or veterinarily active ingredients. Thus the limp dry envelope may for example be rolled up for introduction through the throat but will swell up and therefore be retained in the stomach for sustained release of the active ingredient therein.

14 Claims, 2 Drawing Sheets

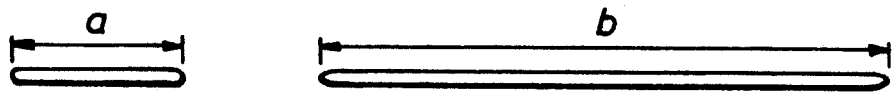
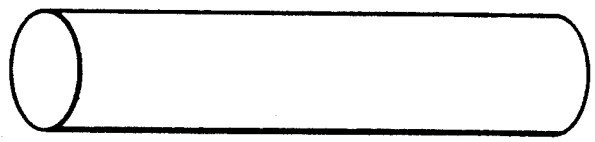
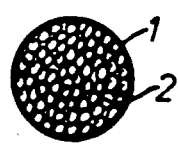
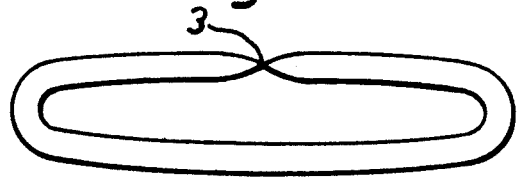
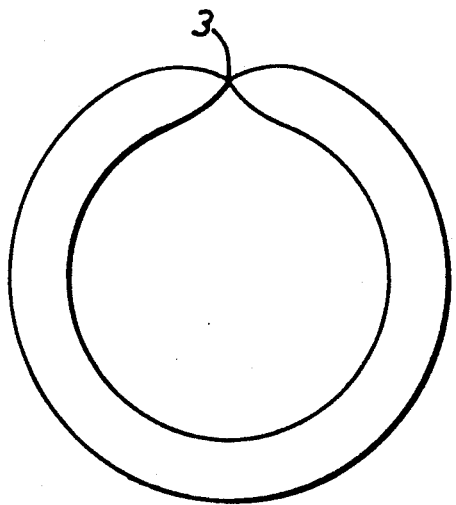

HYDROGEL CONTAINING ENVELOPES

This application is a continuation of application Ser. No. 07/229,725, filed on Aug. 5, 1988, now abandoned, which is a continuation of Ser. No. 06/818,076 filed Jan. 13, 1986 now abandoned, which is a continuation of Ser. No. 06/585,541 filed Mar. 2, 1984 now abandoned.

This invention relates to hydrogel-containing envelopes.

Hydrogels are swellable by aqueous media and their use as absorbents of water or water vapour is well known. Thus for example granules of hydrogel, either free or in a water-permeable or porous bag, may be placed in containers for apparatus. The hydrogel granules absorb any water or water vapour entering the container and thus maintain a dry atmosphere for the apparatus therein. Further hydrogels may be used as absorbents in articles of personal hygiene, for example tampons, incontinence pads, diapers as suggested in British Patent Specification No: 2100269A.

In addition it is known to use hydrogels as carriers, excipients, or delivery agents for active, e.g. pharmaceutical, veterinary, ingredients. There are many treatments where sustained release of active ingredient from for example orally administered pharmaceutical or veterinary compositions is desirable. There has been much interest in the use of hydrogels in the preparation of sustained release compositions whereby the active ingredient is released gradually from the composition. Thus U.S. Pat. Nos: 3,551,556 and 3,689,634 describe sustained release drug-containing compositions comprising the drug and a hydrogel through which the drug is released. U.S. Pat. No: 4,340,491 describes a pouch for the controlled release of active ingredient, in this case principally of ingredient for swimming-pool chlorination, wherein the pouch comprises a sealed envelope of water-insoluble polyvinyl alcohol hydrogel. The e.g. chlorination agent is thus released through the hydrogel walls of the pouch envelope over a long period of time when the pouch is immersed in water. Sustained release preparations comprising an active ingredient and a hydrogel have also been described in British Patent Specifications Nos: 2047093A, 2047094A, 2090264A and 2108517A.

Also in the generally medical field it is known to use hydrogels in wound dressings, where the hydrogels are applied over the wounds to protect them from the external environment. Suitable hydrogels for use in wound dressings are described for example in G.B. 2108517A. Also European Patent Specification No: 0031018 (A1) describes covering material for, for example a wound, wherein a slab of swollen hydrogel material is provided, at least on the side to be in contact with the wound, with a permeable membrane. In wound dressings of this type wound exudate is absorbed by the hydrogel.

It has now been found that considerable benefits to different applications may be obtained by having a particulate hydrogel contained in an envelope, and having a particular mechanical relationship between the external volume of the swollen hydrogel and the internal volume of the envelope.

According to the present invention there is provided an envelope having flexible, water-permeable or porous walls and a given maximum non-stretched internal volume and containing a quantity of particulate water-insoluble hydrogel in the closed envelope wherein the volume of the quantity of hydrogel when fully swollen at 20° C. amounts to at least 66% of the given maximum non-stretched internal volume of the envelope but is insufficient when fully swollen at 20° C. to rupture the envelope.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein;

FIG. 1A shows the width and length dimensions of a flat tube or fabric;

FIG. 1B shows the tube of FIG. 1A as a firm cylindrical package with ends closed and hydrogel present therein and swollen as a result of contact with water;

FIG. 1C is a cross section of the tube of FIG. 1B as it is made of fabric material 1 and as it contains swollen hydrogel particles 2;

FIG. 2A shows an unswollen hydrogel containing tubular device of Example 6 whose ends are stitched together;

FIG. 2B is a view of the swollen hydrogel containing tube of FIG. 2A;

Figure 3A:
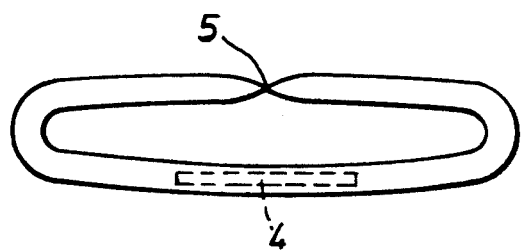
FIG. 3A is a view of the unswollen, dry tubular, hydrogel containing device of Example 10.

The "maximum non-stretched internal volume" of the envelope according to the present invention is the maximum internal volume of the envelope before the walls of the envelope start stretching. When a flexible-walled envelope is flat it has an internal volume of substantially zero. As material is introduced into the envelope, e.g. by inflation, the internal volume of the envelope will increase, without stretching of the envelope walls, to a maximum. Beyond this maximum non-stretched internal volume any further increase in the internal volume of the envelope involves stretching of the material of the envelope walls. Eventually, of course, if too much internal pressure is applied the envelope walls will rupture.

When the hydrogel used according to the present invention contacts water (in liquid or vapour form), it absorbs the water and the hydrogel is thereby caused to swell. According to the present invention the quantity of hydrogel present in the envelope is such that, when fully swollen at 20° C., its volume amounts to at least 66% of the maximum non-stretched internal volume of the envelope. Preferably the fully swollen volume of the hydrogel amounts to at least 100% of the maximum non-stretched internal volume of the envelope. Thus, when the hydrogel is present in the envelope in a non-fully swollen state the envelope is a limp, flexible structure. As the hydrogel absorbs water through the water-permeable or porous walls of the envelope, the hydrogel swells within the envelope and the envelope becomes inflated and more rigid.

When the volume of the fully swollen hydrogel amounts to the minimum 66% of the maximum non-stretched internal volume of the envelope even when the hydrogel is fully swollen the envelope according to the present invention will not be fully rigid though it will be substantially more rigid and of greater size than the non-fully swollen version. Preferably though, as mentioned above, the fully swollen hydrogel should have a volume amounting to at least 100% of the maximum non-stretched internal volume of the envelope. In this way, when the hydrogel has swollen, the envelope according to the present invention has substantially its maximum volume. The rigidity of the envelope will increase as the internal pressure of the envelope increases, though of course the degree of swelling should not be so great that the envelope itself is ruptured.

The envelope according to the present invention has different uses. For example the envelope may be used as an absorbent of liquid water or of water vapour, particularly in locations where the presence of such water is deleterious. Thus for example in homes where condensation occurs or in cars where drips tend to occur envelopes according to the invention, generally in long strip form, can be placed e.g. below the windows prone to condensation to absorb water. As the water is absorbed by the hydrogel, the hydrogel will swell and accordingly the envelope increase in size though it will remain dry to the touch. It can readily be seen when the envelope is fully swollen and thus will no longer absorb further water by the more rigid, inflated (sausage-like) appearance of the envelope. The envelope can then simply be removed and replaced by a fresh one if there remains unabsorbed water.

The removed fully swollen envelope can be heated, e.g. over a radiator, which will cause the water to be desorbed by the hydrogel. The envelope will thus be returned to its limp, flexible form ready for reuse. Alternatively the fully swollen envelope can simply be left because reduction in the humidity of the atmosphere, as tends to occur during the day, will also cause water to be desorbed by the hydrogel making it ready for reuse.

In a similar way the envelopes of the present invention can be used to absorb water vapour from the atmosphere e.g. with a view to preventing condensation occurring again for example in the home or in cars or in ships in dry dock. The envelopes will absorb water vapour from the atmosphere where there is high humidity and it will be desorbed when the humidity is reduced or the heat is increased.

The increase in size and/or rigidity of the envelope according to the present invention as water is absorbed is a function of the degree of swelling and therefore this can be used as a measure of the amount of water absorbed by the hydrogel. The swelling of the envelopes according to the present invention can for example be used to provide a warning that liquid or vapour water levels are rising too high in a particular location. Thus the osmotic pressure which builds up in the envelope according to the present invention as the hydrogel swells can be used to exert pressure to actuate e.g. an alarm mechanism when this pressure exceeds that corresponding to the safe liquid or vapour water levels in the particular location.

With suitable shaping the envelopes according to the present invention may be used as articles of personal hygiene. They could be used by incontinent persons or as tampons or absorbing pads or as sweat bands. With the mechanical relationship of envelope and swollen hydrogel size according to the present invention, the user is readily able to detect by the swollen, inflated nature of the article according to the invention when the article will no longer absorb further although it is still dry to the feel and accordingly when it should be replaced. This is advantageous for example for reasons of comfort.

The envelopes according to the present invention may further be used for the removal of water from mixtures of non-aqueous liquids such as lubricating oils and many organic solvents whereby the water will be absorbed from the mixture to leave the non-aqueous liquid. Using the envelope according to the invention, it can readily be detected by the swollen state of the envelope that it is saturated and needs to be replaced for removal of further water.

In addition to absorbing water vapour from places of high humidity, the envelopes according to the present invention can also be used for humidification in places of low humidity. Thus there can be used a fully inflated envelope according to the present invention wherein the hydrogel is in the fully swollen state. In places of low humidity water will be desorbed from the hydrogel and go into the atmosphere. For this use it is the return of the envelope to its limp, floppy state which indicates that replacement is required. The return to the limp, floppy state shows that the water has been desorbed and accordingly that the envelope is no longer acting as a humidifier.

Because the envelopes according to the present invention are limp and flexible in the substantially dry, non-swollen state while being inflated and substantially rigid in the fully swollen state, they can be introduced into and then be retained in a cavity or container having a narrow entrance and exit. Thus the envelope can be rolled up if necessary to introduce it into the cavity or container and, as long as the cavity or container has sufficient water therein, inside the hydrogel will swell causing the envelope to inflate to a rigid structure so that it is too large to leave via either the narrow entrance or the narrow exit. This is of particular interest in the veterinary and pharmaceutical fields.

Thus the envelopes according to the present invention may be used in the veterinary and pharmaceutical fields; particularly for the administration of sustained release compositions to animals and human beings. It is of course well known to administer veterinarily, pharmaceutically or biologically active ingredients which are released within the animal or human being over an extended period of time following administration. One of the problems associated with such compositions is the ensuring that they are retained within the stomach for a sufficient length of time. Various complicated devices have been proposed to ensure adequate retention in the stomach. Further, while this may not be a problem with animals for slaughter, especially with human patients, it is desirable that the device should, after all the active ingredient has been used up, be itself discharged from the stomach. Suitable veterinarily-active ingredients include anti-infective agents e.g. bacteriocides such as antibiotics and viruscides: anti-parasitic agents, e.g. nematicides, oral vaccines and growth promoting agents, e.g. anabolics, trace elements and vitamins. Trace element preparations may include one or more of magnesium, iron, iodine, copper, cobalt, manganese, zinc and selenium, especially copper, cobalt, selenium or iodine.

Accordingly the present invention also provides an envelope having flexible, water-permeable or porous walls and a given maximum non-stretched internal volume and containing a quantity of particulate water-insoluble hydrogel and a pharmaceutically, veterinarily or biologically active ingredient in sustained release form in the closed envelope wherein the volume of the quantity of hydrogel when fully swollen at 20° C.

amounts to at least 66% of the given maximum non-stretched internal volume but is insufficient when fully swollen at 20° C. to rupture the envelope.

This envelope, in the non-swollen state, can simply be rolled up if necessary and swallowed by the patient or forced down the throat of an animal being treated by a conventional means such as a bolus gun. In the stomach water traversing the water-permeable or porous walls of the envelope will be absorbed by the hydrogel from the stomach juices and accordingly the envelope will swell up in the stomach to its inflated form. Accordingly there it will be retained within the stomach during the sustained release of the active ingredient. Thus the present invention offers a very simple solution to the problem of retention of sustained release compositions in the stomach.

It may be convenient in some applications, for ease of administration, to have the envelope contained in a second outer package which provides some rigidity to the unswollen floppy form of the device. This outer package can ease administration by making it more easy to swallow. The outer package subsequently ruptures by degradation of its adhesive, stitching or of its material or merely under the pressure exerted by the envelope when it swells inside. For example a paper tube, a collagen skin or a plastics film with protein adhesive all provide suitable exteriors to enable the devices to be swallowed or placed in position more easily.

Envelopes according to the present invention can also be used as slimming aids. Thus the envelopes, which in this case need not contain any pharmaceutically active ingredient, can be swallowed by someone wanting to slim. The envelope will swell and be retained in the human stomach to provide a feeling of fullness and thus reduce appetite.

A yet further application of the present invention is in the providing of self-erecting three dimensional structures. These structures may be of any desired shape. The structures can comprise a single envelope according to the invention or can comprise a plurality of compartments joined together, each compartment having a given maximum non-stretched internal volume and containing a quantity of particulate water-insoluble hydrogel wherein the volume of the quantity of hydrogel when fully swollen at 20° C. amounts to at least 66%, preferably at least 100%, of the given maximum non-stretched internal volume but is insufficient when fully swollen at 20° C. to rupture the compartment. These structures will be self-erecting when wetted, e.g. in the rain or by immersing or spraying with water. In this way large rigid structures may be obtained. Of course the structures according to the present invention have to be maintained in wet conditions if they are to stay sufficiently rigid. Thus they will generally be used for the rapid erection of underwater or floating structures which have to be effectively the same density as water for many survival, military and engineering applications. For example the structures can be used in fish farms or as floating booms for enclosing oil spills or in providing inflatable anchors, lightweight diving-bells. Indeed there may be provided self-inflating tanks which, in the presence of water, provide a rigid enclosing structure for liquids, e.g. crude oil or organic solvents, which do not penetrate the water in the tank. Alternatively if it is desired to house an aqueous liquid in the tank, the tank needs to be provided with a water impermeable lining.

Furthermore the present invention provides a method of purifying sea-water. In this embodiment a plurality of envelopes according to the present invention may be contacted with sea-water and they will thus absorb water from the sea. With some hydrogels some concentration of the water occurs by the selective absorption process. The envelopes thereby swollen are drained of non-absorbed water and contained in a system such that, under exposure to sunlight, they will be heated, e.g. by the sun, causing absorbed water to be desorbed by the syneresis or evaporation from the hydrogel. For most efficient heating of the hydrogel the envelopes are preferably provided with a black body covering. The desorbed water from the hydrogel, which will be pure water, is then condensed e.g. for drinking. Suitably the water is condensed in a tank below the water level and therefore cooled by the body of water. This process provides an upside down distillation in which the liquid sea-water being distilled is held in an upper immobile gelled form (having a large surface area corresponding to that of the surface of the swollen hydrogel particles) with the condenser underneath. This allows simple advantage to be taken of the natural arrangement of the hot sun above and the cooling waters of the sea below. Additionally, to provide movement of the air over the devices and to enhance mass transfer of the water from the evaporator to the condenser, a fan to provide a flow of air over the devices may be provided. This apparatus provides an efficient process for producing potable or processed water from salt solution and has a very low energy consumption. It is suitable for small scale emergency water generation (e.g. for use in lifeboats) or for large scale desalination plants.

Any suitable hydrogel may be used in the envelope according to the present invention. The hydrogel used will generally be one which on swelling absorbs more than 40% of its dry weight of water without dissolution. The degree of swelling however is preferably between 150% and 1000% by weight though swellings of higher or lower degree are obtainable and usable. The hydrogel used is suitably one which exhibits syneresis, i.e. one which has the property of undergoing a substantially greater level of swelling in an aqueous medium at 0° C. than at a 100° C. Accordingly water absorbed at lower temperatures will be spontaneously desorbed at the temperature of the hydrogel increased.

The hydrogels can be of natural or synthetic organic or inorganic material. They are normally made of water soluble backbone materials which are rendered insoluble by the introduction of covalent crosslinks e.g. addition polymers of hydroxy alkyl(meth)acrylates, methyl vinyl ether, (meth)acrylamide, N-vinyl pyrrolidone, (meth)acrylic acid and its salts, N-vinyl and C-vinyl pyridines and salts thereof with poly(meth)acrylates such as glycol dimethacrylate. There may also be used crosslinked natural polymers such as collagen or starch and cellulose derivatives and crosslinked synthetic polymers such as polyvinyl alcohol may be used.

Preferably there is used as hydrogel a crosslinked poly(ethylene glycol or ethylene oxide). Suitable crosslinked materials can be prepared by reacting poly(ethylene oxide) or poly(ethylene glycol) with a polyol (e.g. 1,2,6-hexantriol) and a polyisocyanate (e.g. diphenylmethane 4,4'-diisocyanate). Further there may be used insoluble domains (block copolymers of e.g. polyethylene oxide with water-insoluble urethane blocks) or materials rendered insoluble by entanglement crosslinking (high molecular weight poly(ethylene oxides)) with divinylbenzene or by crystallinity (cellulosic materials).

The hydrogel used according to the present invention is in particulate form. Generally the hydrogel will be in granular, powder, strip, fibre or foamed form. The particles of the hydrogel must of course be large enough to be retained within the porous or permeable envelope even when they are in their dried, unswollen condition. Thus the average dry particle size will generally be at least 1% larger, and preferably at least twice (more preferably at least 10%) the size of the pores in the surrounding envelope. The particulate hydrogels for use in the present invention may conveniently be prepared by contacting the hydrogel with water and subjecting the swollen hydrogel to shear stress such that it is comminuted to particles as described in British Patent Specification No: 2100269A.

It can be advantageous for the hydrogel particles according to the present invention to be in expanded form. Thus for example in the case of polyethylene oxide particles water present may react with added diisocyanate to liberate carbon dioxide gas to produce an expanded polymer. This can be advantageous firstly because the polyethylene oxide in this way does not require a preliminary drying operation and, in addition, the resulting expanded polymer may be more readily swollen and comminuted.

When the envelope according to the present invention also contains pharmaceutically, veterinarily or biologically active ingredient in sustained release form, there may be mixed with the hydrogel particles particles containing the active ingredient in a sustained release form for example as described in U.S. Pat. Nos. 4,150,108 and 4,221,779. Many formulations for the sustained release of active ingredients in this way are known. Alternatively the active ingredient may be present, in sustained release form, in the hydrogel particles themselves. Suitable such compositions are described for example in British Patent Specifications Nos: 2047093A, 2047094A and 2108517A.

The envelope according to the present invention is sized such that the volume of the quantity of hydrogel contained in it, when fully swollen (including any spaces inside or between hydrogel particles) at 20° C., amounts to at least 66% of the maximum non-stretched internal volume of the envelope. The ratio of envelope size to external volume of fully swollen hydrogel contained therein may vary according to the proposed use of the envelope. Thus when the rigidity of the swollen envelope is important the non-stretched internal volume of the envelope will generally be at least approximately equal to the external volume of the swollen hydrogel. Thus the envelope material will be taut around the swollen hydrogel. In some applications, where mechanically very rigid structures are required, the maximum external volume of the fully swollen hydrogel will be greater than 100% of the maximum non-stretched internal volume of the envelope. Of course in this case the envelope must be made of material having sufficient strength to withstand the forces of compressed swollen hydrogel within. In applications where rigidity is less important the volume of the swollen hydrogel may be less than 100% of the maximum non-stretched internal volume of the envelope. Generally speaking the volume of the quantity of hydrogel, when fully swollen at 20° C., amounts to at least 90 to 110%, most preferably at least 95 to 105%, of the maximum non-stretched internal volume of the envelope.

The envelope is of porous or permeable material to allow the water or water vapour to reach the hydrogel within. Further the envelope material must be flexible so that the envelope is limp and flexible when the hydrogel is unswollen and of limited extensibility to obtain the required rigid structure when the hydrogel is swollen within the envelope. The actual material of the composition of the envelope will depend upon the use to which it is to be put and the properties e.g. as regards strength required. If a high degree of strength is not required then the envelope may simply be of a textile mat such as paper or felt. For stronger structures knits, weaves and braids may typically be used. These may utilise natural or synthetic fibres of organic or inorganic materials, e.g. biodegradable natural proteins, fibrillated polypropylene, polyester continuous filament, metal wire, fibreglass and carbon fibre. Alternatively a continuous flexible sheet of plastics material or rubber, into which micro- or macropores have been introduced, may be used. The envelope will of course be closed to prevent escape of the hydrogel. This closing may simply be by stitching, glueing or by heat sealing for example.

The shape of the envelope according to the present invention will vary according to the intended use. As mentioned above for the absorption of e.g. water vapour or condensation the envelope may suitably be in the form of a strip which, on hydration of the hydrogel, swells up to form a cylinder. Also in the case of articles of personal hygiene and indeed for three dimensional structures which are self-erecting the shape of the envelope will very much be determined by the particular end use. When the envelope is one for introduction into a cavity or container having a narrow entrance and exit, a most convenient shape is that of a toroid. Thus the envelope according to the invention may be formed from a tube, e.g. tubular braid, the hydrogel particles inserted and then the two ends brought together to form a toroid, loop or ring shaped. The limp flexible structure when the hydrogel is substantially unswollen can readily be e.g. rolled up for introduction through the narrow entrance of the cavity or container. Once inside however the envelope absorbs water and the volume filling structures thereby obtained are even less likely to be able to get out through the narrow entrances or exits.

If it is desired that the envelope and hydrogel material be discharged from the stomach after the e.g. veterinarily or pharmaceutically active ingredient has been released, the envelope may be of a slowly dissolving material. In this way the hydrogel particles will be released after dissolution of the envelope and will thus be passed out from the stomach. Such bio-absorbable materials are well known in the food, pharmaceutical and surgical fields, e.g. collagen, various cellulosic derivatives and poly(lactic) or poly(glycolic) acids.

The invention is further illustrated, by way of Example, with reference to the following Examples.

EXAMPLE 1

A polyethylene oxide hydrogel was prepared by the method described in Example 1 of British Patent Specification No. 2 047 093A by reacting 50 g polyethylene oxide ($\overline{M}_n$=7350) with 0.684 g 1,2,6-hexanetriol and 3.795 g bis-(4-isocyanatocyclohexyl) methane (Hylene W ex du Pont) corresponding to a molar ratio of 1:0.75:2.125 respectively.

The fully swollen hydrogel was then comminuted in a domestic liquidiser (Kenwood "Chef") for five minutes at a shear rate of 13500 rpm and a volume ratio of 1:1 of swollen polymer to water. The conditions were selected to produce the maximum yield of particles of the requisite size for use in the fabric container used in this example.

The particles were then filtered off, washed thoroughly with boiling water, and then dried by a through current of air.

One end of a fabric tube was stitched closed with polyester thread. The fabric tube was a 77 cm. length circularly knitted tube, 2.5 cm. flat width, made on a 10 gauge flatbed machine from 2 ends of textured polyester yarn (2/167 Tex) threaded through 15 needles front and back. 40 g dry hydrogel particles (840–1760 microns) were introduced into the fabric tube and the open end of the tube was stitched closed. At this level of packing the tube was of generally circular cross-section but could be wound round a 7.5 cm. diameter former with little resistance.

When the device so formed was contacted with water, 140 ml. water were absorbed by the hydrogel. The outside of the swollen device was "dry" to the touch and the device had swollen to a firm cylindrical package with resistance to bending.

The swollen device was left to dry in the air whereby the swollen shape was lost. Then the device was re-used for absorption of water. The cycle of absorption of water followed by air drying was carried out repeatedly without detectable alteration of the water uptake. Drying of the swollen device was on occasion speeded up by hanging it in a current of warm air and at other times, to reduce the drying time still further, by immersion in boiling water prior to drying.

FIG. 1 accompanying the present specification illustrates diagrammatically the device according to Example 1. Thus FIG. 1A illustrates a fabric tube of flat width a and length b which on having hydrogel inserted inside, the ends closed and contacted with water swells to form a firm cylindrical package as shown in FIG. 1B. FIG. 1C is a cross-section through the cylindrical package of FIG. 1B showing the fabric tube material 1 and the swollen hydrogel particles 2 inside.

EXAMPLE 2

A device was made similar in all respects to that described in Example 1 except that the particulate charge was prepared from a polyethylene oxide hydrogel obtained by the reaction of 60 g polyethylene oxide ($\overline{M}_n = 6427$) with 2.75 g of a commercial di-isocyanatodiphenyl methane (Suprasec DND ex I.C.I.) containing some higher functionality isocyanates. These proportions correspond to a 10% excess of the di-isocyanate from a 1:1 molar ratio.

The water uptake of the hydrogel particles in the device so formed was of the same order as those of Example 1 and the swelling and drying behaviour were also similar.

EXAMPLE 3

Small amounts of water present in polyethylene oxide will also react with added di-isocyanates liberating carbon dioxide gas to produce an expanded polymer. This can be advantageous in the production of absorbent particles in that the polyethylene oxide does not require a preliminary drying operation and the resulting expanded polymer is more readily swollen and comminuted.

100 g polyethylene oxide ($\overline{M}_n = 6427$) with a water content of 0.4% were reacted with 7.7 g di-isocyanatodiphenyl methane. The amount of di-isocyanato-diphenyl methane was sufficient to react with the water and leave an excess of 10% above a 1:1 molar ratio.

The resulting expanded polymer was comminuted as in Example 1, except that the swollen polymer-water mixture was subjected to shearing for 30 seconds instead of 5 minutes.

Using the particles thus obtained and a polyester braid tube, 2.0 cm. flat width, formed on a 48 spindle machine using 5/115 Tex yarn, the ends of which were closed by heat sealing, there was made a device as in Example 1. The water uptake of the device was 180 ml. which was unaltered by repeated drying and re-absorption of water.

EXAMPLE 4

Hydrogel particles were obtained from a cross-linked polymer, prepared by reacting polyethylene oxide ($\overline{M}_n = 7450$), 1,2,6-hexane triol and acrolein tetramer as described in Example 6 of British Patent Specification No. 2 100 269A. Using a knitted nylon tube, the ends of which were closed by stitching with nylon thread, there was obtained a device similar to that described in Example 1. The absorption and drying characteristics of the device obtained were found to be similar to those of the device of Example 1.

EXAMPLE 5

A device was made by the method of Example 1 except that the particulate hydrogel charge was prepared by reacting polyethylene oxide ($\overline{M}_n = 4360$), 1,2,6-hexane triol and bis-(4-isocyanatocyclohexyl)methane in a 1:0.75:1.5 molar ratio.

The device absorbed 280 ml. water without feeling wet to the touch and a drying-water absorption cycle was repeated frequently without apparent change in effectiveness.

EXAMPLE 6

A circular tube of flat width 2 cm. was knitted on a 10 gauge flat bed machine having ten needles front and back threaded with 3 ends of pale blue coloured polyester yarn (Dacron ex du Pont) of 1/150 denier count.

18 g of polyethylene oxide hydrogel particles obtained as described in Example 1 were inserted into 60 cm. length of the tube, the ends of which were overlapped by 2 cm and stitched together with a polyester (Dacron) yarn to form a ring (like a headband).

When this device was contacted with water 60 ml. water were absorbed into the device. The swollen device thus formed was in the form of an inflated toroid which felt cool but not moist to the skin. This tubular ring was air dried and, after drying, it absorbed 50 ml. of a 3% (weight by volume) salt solution. The ring was then immersed in hot water, squeezed free of excess water and dried in warm air. Repetition of this operation (i.e. salt water absorption to drying) did not impair the absorption capacity of the device.

The device of this example is illustrated in FIG. 2 of the accompanying drawings wherein FIG. 2A shows diagrammatically the form of the unswollen device whereas FIG. 2B shows diagrammatically the form of the swollen device of this example. In both FIG. 2A and FIG. 2B 3 denotes the stitching of the ring together.

EXAMPLE 7

A ring device was prepared in the manner of Example 6 with the following modifications; the circular tube used was knitted using two ends of dark blue coloured crimped nylon yarn threaded through the knitting machine needles. The length of the tube used was 56 cm. and the ring was completed by stitching together with nylon thread a 1 cm. overlap of one end of the tube to one end of a 4 cm. length of 2 cm. wide elasticated strip. The other end of the tube was joined to the other end of the elasticated strip. Thus in the ring of this example there was a 2 cm. long extensible insert.

The results of absorption of water and of salt solution and of drying in this example did not differ from those of the ring described in Example 6.

EXAMPLE 8

40 g of particulate polyethylene oxide/di-isocyanato-diphenyl methane hydrogel as described in Example 3 were introduced into a polyester braid tube, length 38 cm., also as described in Example 3. The two ends of the charged tube were placed together to form a 1.5 cm. overlap and fused under controlled temperature and pressure conditions to form a ring device.

When the device was placed in water, it swelled into a doughnut-shape having an outer diameter of 14 cm. and with the diameter of the swollen braid tube in the ring being 2.5 cm.

EXAMPLE 9

A tube of 3.5 cm. flat width was knitted on a circular weft knitting machine (No. 3 "Lilliput" machine) using 2 ends of textured polyester yarn (2/167 Tex) and 66 needles. A length of 45 cm. of this tube was filled with 45 g of hydrogel particles prepared as described in Example 3. An annular device was made by stitching together with cotton threads the two ends overlapping each other by 2 cm.

When the device was fully swollen there was formed a ring having an outer diameter of 16 cm. The diameter of the swollen tube forming the ring was then 3.5 cm.

EXAMPLE 10

A tube was knitted as in Example 9 using a single end of the polyester yarn and 58 needles producing a 2.5 cm. flat width tube. To 22 cm. of this tube were added 16.5 g of hydrogel particles prepared as described in Example 1 and a 3 cm. length of 0.7 cm. diameter steel rod weighing approximately 20 g. With a 1 cm. overlap of the ends, the ends of the tube were stitched together using a polyester braid fishing line to form a ring device. On immersion in water, the device was swollen into a doughnut-shape.

Figure 3B:
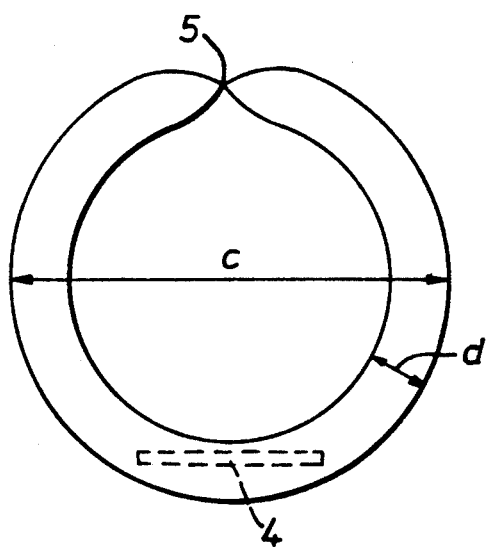
FIG. 3B is a view of the swollen tubular device of FIG. 3A.

The embodiment of this example is illustrated in FIG. 3 of the accompanying drawings wherein FIG. 3A shows the unswollen, dry device and FIG. 3B shows the device after swelling in water. In FIG. 3 the steel rod is shown as 4 and the stitching of the ring device as 5. The overall diameter c of the ring is 7 cm. and the diameter of the swollen braid d is 2.2 cm. in FIG. 3B The presence of the steel rod in the device of this example can be used to make the position of the device in for example an animal's stomach more readily detected since the position of the metal can be detected from the outside of the animal.

EXAMPLE 11

The dry device of Example 10 shown in FIG. 3A was inserted into a tube of cellulose film to provide a smooth outer surface.

EXAMPLE 12

The dry device of Example 10 shown in FIG. 3A was inserted into a sausage skin to provide a smooth outer surface.

EXAMPLE 13

A tube was knitted as in Example 9 but to produce a 2.5 cm. flat width. 22 cm. of this tube was charged with 20 g of hydrogel particles prepared by the method described in Example 1 and with 10 discs incorporating 20% pyrimethamine in dihydropyran polymer prepared by the method described in Example 1 of U.S. Pat. No. 4,221,779. The overlapped ends of the tube were stitched together to form a ring device.

The ring device was swollen in water to the dimensions of the ring of Example 10 shown in FIG. 3B of the accompanying drawings.

It is reported by Judge et al (Sustained release implants in the chemotherapy of experimental rodent malaria II, Annals of Tropical Medicine and Parasitology, Vol. 75, No. 5, 511–519 (1981)) that one disc as described above implanted subcutaneously protected mice against challenge with *Plasmodium berghei* (N strain) for more than 20 weeks.

EXAMPLE 14

A polyester braid tube as described in Example 3 and of length 16.0 cm. was heat sealed at one end. 13 g of hydrogel particles prepared as described in Example 2 were introduced through the open end of the tube which was then closed by heat sealing.

When contacted with water, the tube swelled to form a rigid cylinder. The measurements of the device were as follows:

|  | Dry tube (flexible) | Swollen tube (rigid) |
| --- | --- | --- |
| Length | 11.5 cm. | 10.5 cm. |
| Width | 2.4 cm. | 2.5 cm. |

The volume of the gel in the dry tube was 33.5 ml while the internal volume of the swollen tube was 49.0 ml.

EXAMPLE 15

A knitted tubed as described in Example 1 of length 24 cm. was heat sealed at one end. 20 g of hydrogel particles prepared as described in Example 2 were introduced through the open end of the tube which was then stitched closed with polyester yarn.

On contacting with water the tube of the device swelled up to a straight cylindrical shape. The cylinder had some resistance to bending and returned to a straight cylindrical shape on removal of the bending forces.

The measurements of the device of this example were as follows:

|  | Dry tube | Swollen tube |
| --- | --- | --- |
| Length | 22.0 cm. | 20.0 cm. |
| Width | 2.6 cm. | 2.7 cm. |

The volume of the gel in the dry tube was 43.0 ml. while the internal volume of the swollen tube was 114.0 ml.

EXAMPLE 16

A bag made from an 8 gauge single weft knitted fabric using 3 ends of 2/167 Tex polyester filament yarn and in the shape of a short cylinder 16 cm. in diameter and 7 cm. high was charged with 150 g of coarse (greater than 2000 microns) hydrogel particles prepared by the method described in Example 5.

The bag absorbed 1 liter of 3% (weight by volume) salt solution before it was near its limit of absorption. The bag thereby swollen did not feel wet to the skin. Immersion of the swollen bag in boiling water to remove the salt solution, followed by drying in hot air did not change the water absorption of the hydrogel.

EXAMPLE 17

There are introduced into a bag made from knitted fabric as described in Example 16 in the shape of a square cushion, 45 cm. side length, 8 cm. depth, 1.5 kg. of the coarse hydrogel particles used in Example 16. A cushion thereby obtained readily absorbed 3 liters of the salt solution without feeling wet to the touch.

EXAMPLE 18

0.85 mole freshly distilled methyl methacrylate was mixed with 0.14 mole hexaethoxylated hydroxyethylmethacrylate, 0.01 mole trimethylol propane trimethacrylate and 0.023 mole benzoyl peroxide. The mixture was warmed to 65° C. until reation was initiated whereafter the reaction was allowed to continue without further heating for 2 hours to give a solid gel. This gel was broken down into particles and packed very tightly into a tubular container. When in contact with water the gel swelled to twice its original size.

I claim:

1. A method of treating animals which method comprises administering to the animal an envelope having flexible water-permeable or porous walls and a given maximum non-stretched internal volume and containing a quantity of particulate water-insoluble hydrogel and a veterinarily active ingredient in sustained release form in the closed envelope wherein the volume of the quantity of hydrogel when fully swollen at 20° C. amounts to at least 66% of the given maximum non-stretched internal volume but is insufficient when fully swollen at 20° C. to rupture the envelope.

2. A method according to claim 1 wherein the animal is a ruminant.

3. A method of treating a human patient which method comprises administering to the patient an envelope having flexible water-permeable or porous walls and a given maximum non-stretched internal volume and containing a quantity of particulate water-insoluble hydrogel and a pharmaceutically active ingredient in sustained release form in the closed envelope wherein the volume of the quantity of hydrogel when fully swollen at 20° C. amounts to at least 66% of the given maximum non-stretched internal volume but is insufficient when fully swollen at 20° C. to rupture the envelope.

4. A device for sustained release of an active ingredient in the stomach of a human or animal, which device comprises an envelope having flexible water-permeable and porous walls of perforated plastic, knitted, braid or woven material, the envelope containing particulate water-insoluble hydrogel in a pharmaceutically, veterinarily or biologically active ingredient in sustained release form in the closed envelope wherein the volume of the hydrogel when fully swollen in water at 20° C. amounts to at least 66% of the maximum non-stretched internal volume of the envelope and is sufficient to retain the device within the stomach of the human or animal during the sustained release of the active ingredient but is insufficient when fully swollen in water at 20° C. to rupture the envelope.

5. The envelope according to claim 4, wherein the quantity of hydrogel when fully swollen in water at 20° C. amounts to at least 100% of the given maximum non-stretched internal volume.

6. The envelope according to claim 4, wherein the hydrogel is a crosslinked polyethylene glycol.

7. The envelope according to claim 4, which contains a mixture of hydrogel particles and particles of active ingredient in sustained release form.

8. The envelope according to claim 4, wherein the active ingredient in sustained release form is contained in the hydrogel particles.

9. The envelope according to claim 4, wherein the quantity of hydrogel when fully swollen in water at 20° C. ranges from 90 to 110% of the given maximum non-stretched internal volume of the envelope.

10. The envelope according to claim 4, wherein the average particle size of the hydrogel particles is at least 1% larger than the pores of the surrounding envelope.

11. The envelope according to claim 10, wherein said average particle size is at least twice the size of the pores of the surrounding envelope.

12. The envelope according to claim 4, wherein the hydrogel is one that upon swelling absorbs more than 40% of its dry weight of water without dissolution.

13. The envelope according to claim 12, wherein the degree of swelling of the hydrogel ranges between 150 and 1000% by weight.

14. The envelope according to claim 4, which is in the form of a toroid.

* * * * *